United States Patent [19]
Yokoo et al.

[11] Patent Number: 5,981,756
[45] Date of Patent: Nov. 9, 1999

[54] DEUTERATED 2-ADAMANTYLAMINO-5-NITROPYRIDINE, ORGANIC NONLINEAR OPTICAL MATERIAL CONTAINING THE COMPOUND, AND PRODUCTION METHOD OF THE COMPOUND

[75] Inventors: Atsushi Yokoo, Zama; Itaru Yokohama; Satoru Tomaru, both of Mito; Toshikuni Kaino, Sendai, all of Japan

[73] Assignee: Nippon Telegraph and Telephone Corporation, Japan

[21] Appl. No.: 08/971,026

[22] Filed: Nov. 14, 1997

[30] Foreign Application Priority Data

Nov. 15, 1996 [JP] Japan ..................................... 8-304953

[51] Int. Cl.$^6$ ............................ C07D 213/02; G02F 1/35
[52] U.S. Cl. ............................................... 546/307
[58] Field of Search ............................................... 546/307

[56] References Cited

FOREIGN PATENT DOCUMENTS 63-21627  1/1988  Japan .
1-124834  5/1989  Japan .

Primary Examiner—Zinna Northington Davis
Attorney, Agent, or Firm—Fitch, Even, Tabin & Flannery

[57] ABSTRACT

Of hydrogen atoms constituting 2-adamantylamino-5-nitropyridine, at least hydrogen atom of N—H part is substituted with deuterium to obtain a deuterated AANP. An organic optical material is made from the deuterated AANP. Content of the deuterated AANP in this case is preferably more than 25%. With this method, an organic nonlinear optical material can be provided for devices having a large wavelength conversion efficiency in wavelength conversion relating to optical communications wavelength region, particularly at and around 1.55 $\mu$m wavelength.

5 Claims, 9 Drawing Sheets

(a)

(b)

(c)

(d)

(IN THE FIGURE, D DENOTES DEUTERIUM)

DEUTERATED 2-ADAMANTYLAMINO-5-NITROPYRIDINE, ORGANIC NONLINEAR OPTICAL MATERIAL CONTAINING THE COMPOUND, AND PRODUCTION METHOD OF THE COMPOUND

BACKGROUND OF THE INVENTION

1. Field of the Invention

The present invention relates to an organic nonlinear optical material which can be used in a highly efficient wavelength conversion device for use in optical communication wavelength bands, to 2-adamantylamino-5-nitropyridine which is suitable for use in the optical material, and to a production method thereof.

2. Description of the Prior Art

As well known, organic nonlinear optical materials are drawing attention as materials for achieving highly efficient wavelength conversion devices. 2-Adamantylamino-5-nitropyridine (hereinafter abbreviated to as AANP) is known to be useful as a material of a wavelength conversion device because the compound has a large second order nonlinear optical coefficient (refer to Japanese Patent Application No. 282221/1987 [Japanese Patent Application Laid-open Publication No. 124834/1989]). Since AANP has wavelength conversion characteristics particularly in 1.3 to 1.6 $\mu$m wavelength region, which are optical communications wavelength region, application of this compound is being investigated for measuring instruments utilizing wavelength conversion in optical communications wavelength region.

Main usable wavelength region of AANP are at and around 1.32 $\mu$m wavelength and at and around 1.55 $\mu$m wavelength. At and around 1.32 $\mu$m wavelength, a bulk crystal of AANP has a very high wavelength conversion efficiency of $3 \times 10^{-3}$ (/W) for second harmonic generation (SHG). On the other hand, at and around 1.55 $\mu$m wavelength, the same AANP bulk crystal has only a small wavelength conversion efficiency of $2 \times 10^{-4}$ (/W) for SHG as compared with the value at and around 1.32 $\mu$m wavelength. Therefore, a nearly the same wavelength conversion efficiency at and around 1.32 $\mu$m wavelength has been required for AANP also at and around 1.55 $\mu$m wavelength.

However, no solution for preventing the reduction in wavelength conversion efficiency at and around 1.55 $\mu$m wavelength of the AANP has been found up to now, because the cause of the reduction has not been revealed.

SUMMARY OF THE INVENTION

A primary object of the present invention is to provide AANP having a high wavelength conversion efficiency in optical communication wavelength region, in particular, in wavelength conversion related at and around 1.55 $\mu$m wavelength and an organic nonlinear optical material for devices containing the AANP.

The inventors have conducted intensive studies to solve the above prior art problems and obtained the following findings.

A cause of reduction in wavelength conversion efficiency at and around 1.55 $\mu$m wavelength of the AANP crystal is considered as that the AANP has an absorption loss at and around 1.55 $\mu$m wavelength. In general, when an organic optical material has an absorption loss in an operation wavelength region, it is considered as a method to reduce absorption in the objective operation wavelength region that a hydrogen atom in the molecule of the organic optical material is substituted with deuterium to shift the absorption wavelength.

However, in the case of a nonlinear optical material, wavelength conversion characteristics such as d-coefficient and phase matching wavelength are important for its performance, and in the case of a second order nonlinear optical material, crystallinity of how good quality crystal is obtained is also an even further important factor for the performance of the material.

The wavelength conversion characteristics and the crystallinity of the AANP are probably influenced by deuteration of a hydrogen atom in the molecule. Therefore, deuteration of an optional hydrogen atom in the molecule does not always solve the problem of prior art that is degradation of wavelength conversion efficiency, but it is important to deuterate hydrogen of a specific position.

As shown in FIG. 1, AANP can be divided broadly into three parts, a pyridine ring part (P), an N—H part (N), and an adamantane ring part (AD).

When a hydrogen atom of the pyridine part (P) is substituted with a deuterium, the absorption loss at and around 1.55 $\mu$m wavelength of the resulting compound cannot be reduced, and depression of the crystallinity and shifting of the phase-matching characteristics take place, thus the compound does not have the same applicability as the conventional AANP for wavelength conversion in wavelength region around 1.55 $\mu$m. Further, when a hydrogen atom of the adamantane ring part (AD) is substituted with a deuterium, also the absorption loss at and around 1.55 $\mu$m wavelength of the resulting compound cannot be reduced, and depression of the crystallinity and shifting of the phase-matching characteristics take place, thus the compound does not have the same applicability as the conventional AANP for wavelength conversion in wavelength region around 1.55 $\mu$m. On the other hand, when the hydrogen atom of the N—H (N) part is deuterated, absorption loss at and around 1.55 $\mu$m wavelength can be reduced and the wavelength conversion efficiency can be improved while maintaining the characteristics as a nonlinear optical material.

From the above experiments and investigations of AANP, it has been found that only hydrogen of the N—H part may be deuterated in order to reduce absorption loss at and around 1.55 $\mu$m wavelength and obtain an AANP of improved wavelength conversion efficiency. The present invention has been accomplished on the basis of the above-described findings.

That is, deuterated AANP according to the present invention is characterized in that hydrogen atom of at least the N—H part is substituted with deuterium.

Further, the organic nonlinear optical material according to the present invention comprises 2-adamantylamino-5-nitropyridine, and the 2-adamantylamino-5-nitropyridine contains deuterated 2-adamantylamino-5-nitropyridine with hydrogen atom of at least the N—H part substituted with deuterium.

In the organic nonlinear optical material, it is preferable that the deuterated 2-adamantylamino-5-nitropyridine with hydrogen atom of at least the N—H part substituted with deuterium is contained in an amount of more than 25%.

Still further, a production method of the deuterated 2-adamantylamino-5-nitropyridine according to the present invention is characterized in that 2-chloro-5-nitropyridine and 1-adamantaneamine with hydrogen atom of the amino part substituted with deuterium are reacted, the resulting reaction product is cooled for deposition, the deposit is filtered, washed, dissolved in a solvent, and recrystallized from the solvent for obtaining a granular crystal of deuterated 2-adamantylamino-5-nitropyridine with hydrogen atom of at least the N—H part substituted with deuterium.

Yet further, another production method of the 2-adamantylamino-5-nitropyridine according to the present invention is characterized in that 2-amino-5-nitropyridine with hydrogen of the amino part substituted with deuterium and 1-chloroadamantane are reacted, the resulting reaction product is cooled for deposition, the deposit is filtered, washed, dissolved in a solvent, and recrystallized from the solvent to obtain a granular crystal of deuterated 2-adamantylamino-5-nitropyridine with hydrogen atom of at least the N—H part substituted with deuterium.

Further more, another production method of the 2-adamantylamino-5-nitropyridine according to the present invention is characterized in that undeuterated AANP is heat refluxed in a mixture of tetrahydrofuran (THF) and heavy water to obtain a graular crystal of deuterated 2-adamantylamino-5-nitropyridine with hydrogen atom of at least the N—H part substituted with deuterium.

The above and other objects, effects, features and advantages of the present invention will become more apparent from the following description of embodiments thereof taken in conjunction with the accompanying drawings.

DETAILED DESCRIPTION OF PREFERRED EMBODIMENTS

If absorption loss at and around a wavelength in an organic nonlinear optical material is caused by a vibration absorption of bonds among constituting atoms of the optical material, the absorption wavelength can be changed by replacing one of the constituting atoms with an isotope of different mass. For the case of AANP, since the inventors have found that the absorption at and around 1.55 $\mu$m wavelength is caused by the bond between nitrogen atom and hydrogen atom of the N—H part of AANP, it has become possible to reduce the absorption at and around 1.55 $\mu$m wavelength by substituting hydrogen atom of N—H part with deuterium which is an isotope of hydrogen.

As described above, it is revealed that the absorption loss at and around 1.55 $\mu$m wavelength is caused by the N—H part by deuterating hydrogen atom constituting the molecule and measuring adsorption spectrum thereof(Embodiment 1). And, both of crystallinity, which is an essential characteristic as a nonlinear optical material, and phase matching characteristics of the deuterated AANP have been examined. Embodiments conducted for this purpose are shown below. In Embodiment 2, the relationship between the deuterium substitution position and the crystallinity was determined. Further, in Embodiment 3, the relationship between the deuterium substitution position and the phase matching wavlength was determined.

Embodiment 1

Figure 1:
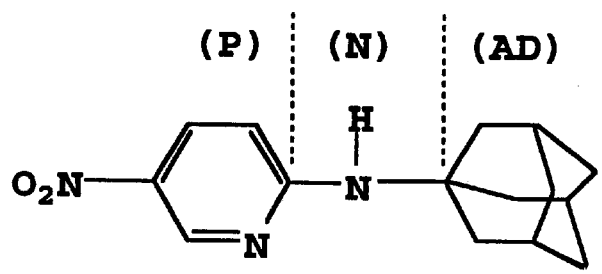
FIG. 1 is a diagram showing a chemical structural formula of prior art AANP.
Figure 2:
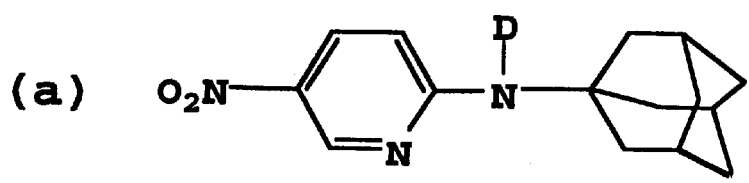
FIG. 2 is a diagram showing a chemical structural formula of the organic nonlinear optical material according to the present invention.
Figure 2:
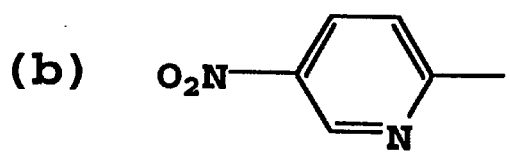
Figure 2:
Figure 2:
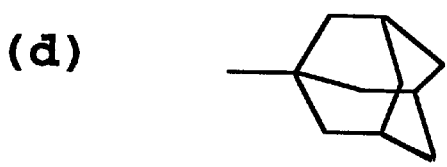

Ten mmole of 2-chloro-5-nitropyridine and 11 mmole of 1-adamantaneamine with hydrogen of the amino part deuterated were dissolved in triethylamine, and heat refluxed for 24 hours under a nitrogen atmosphere to obtain a reaction product. After the reaction solution was cooled to room temperature to completely deposit a product, the product was filtered and washed with cold ethanol. The product was recrystallized using benzene to obtain a granular crystal. The structure of the produced crystal is shown in FIG. 2(a). The produced crystal has an amine structure comprising a nitropyridine part shown in FIG. 2(b), an N—H part shown in FIG. 2(c), and an adamantane part shown in FIG. 2(d), which are linked with each other, which is the AANP according to the present invention of which hydrogen of the N—H part is substituted with deuterium. If the N—H part comprises ordinary hydrogen, it is the prior art AANP as shown in FIG. 1.

The produced crystal was examined by means of NMR and found to contain the AANP with hydrogen of N—H part deuterated in an amount of about 95%.

Figure 3:
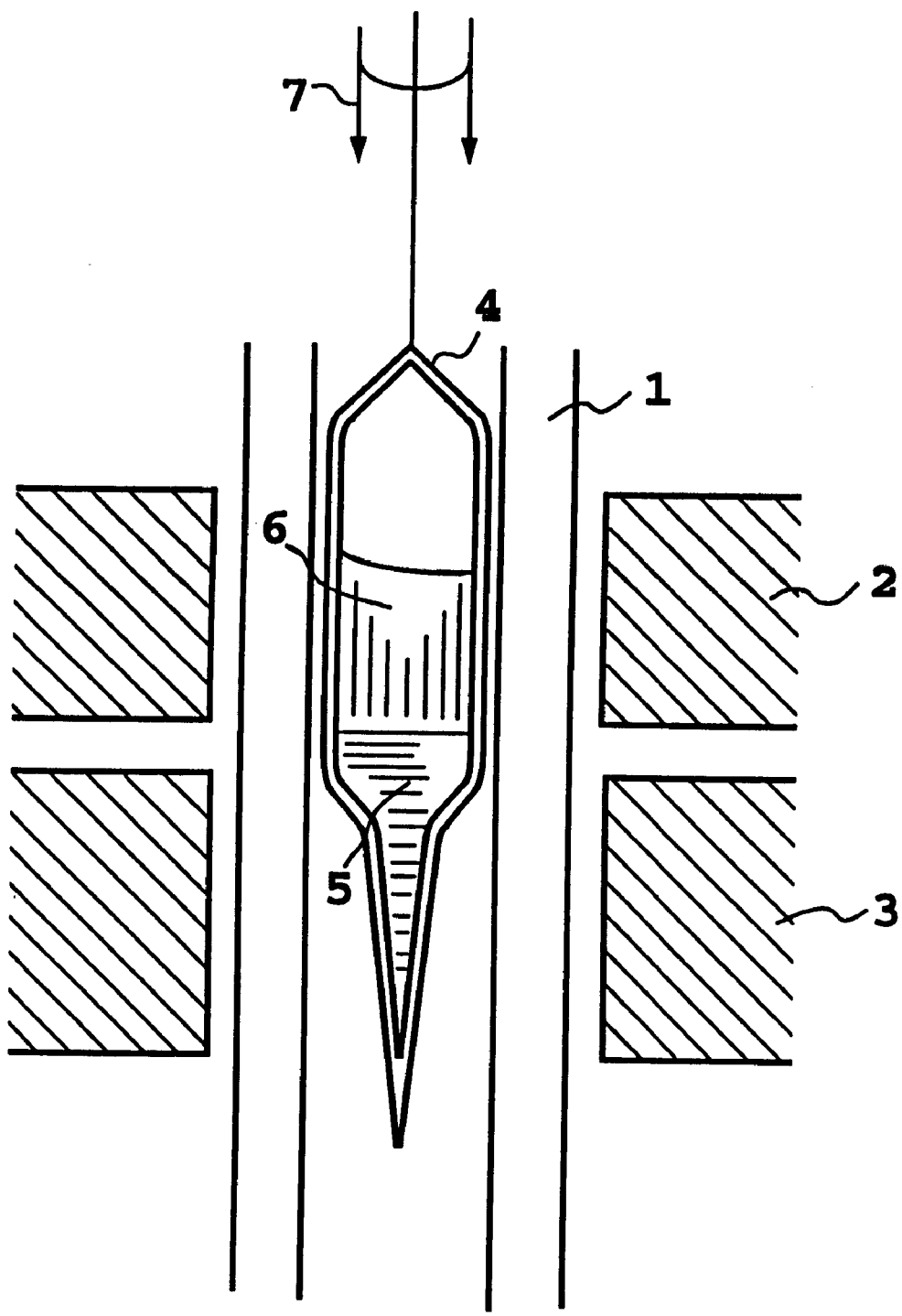
FIG. 3 is a schematic view showing the construction of a single crystal growth apparatus used in the present invention.

A single crystal of the AANP with hydrogen of N—H part deuterated according to the present invention was obtained using the apparatus shown in FIG. 3 and the following procedure. One heater 2 of two heaters in FIG. 3 was set to a temperature of 175° which is 8° C. higher than the melting point (167° C.) of the AANP according to the present invention of which hydrogen of N—H part is substituted with deuterium, and the other heater 3 was set to a temperature of 125° C., 42° C. lower than the melting point. First, a crystal growth glass ampoule 4 was prepared, 10 g of the AANP with hydrogen of N—H part deuterated according to the present invention produced by the above-described method was placed in the ampoule 4, and sealed under a nitrogen atmosphere. The ampoule 4 was slowly moved down at a rate of 1 mm/hr in a core tube 1 of a crystal growth furnace shown in FIG. 3, then the movement of the ampoule 4 was once stopped at the position of the heater 3, gradually cooled down to room temperature at a rate of 5° C./hr, and a grown crystal 6 was taken out. A single crystal 6 was grown almost in the entire ampoule 4, with dimensions of a 12 mm in diameter and about 30 mm in length, which was an AANP single crystal with hydrogen of N—H part deuterated according to the present invention. In the Figure, the reference numeral 7 indicates a pull-down system.

Comparison results showing that absorption at and around 1.55 $\mu$m wavelength is due to the hydrogen of N—H part and showing the effects of the present invention will be described below.

Three types of AANP, the prior art AANP, an AANP with hydrogen of the nitropyridine part deuterated produced using 2-chloro-5-nitropyridine with hydrogen of the nitropyridine part deuterated as a raw material, and an AANP with hydrogen of the adamantane part deuterated produced using 1-adamantaneamine with hydrogen of the adamantane part deuterated as a raw material, were produced, and single crystals were prepared using the same procedure.

Figure 4:
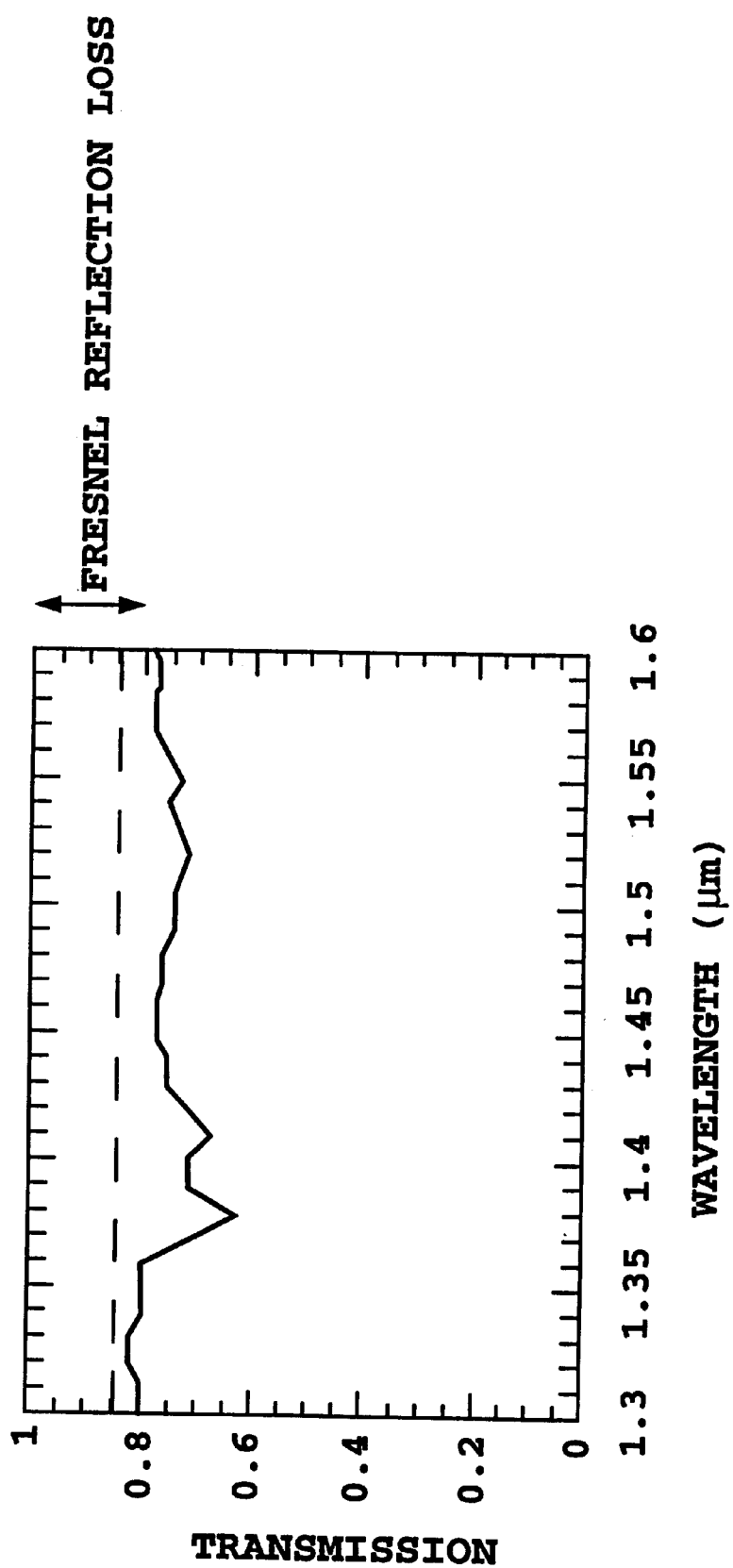
FIG. 4 is a graph showing absorption characteristics of AANP with hydrogen of the N—H part deuterated according to the present invention.
Figure 5:
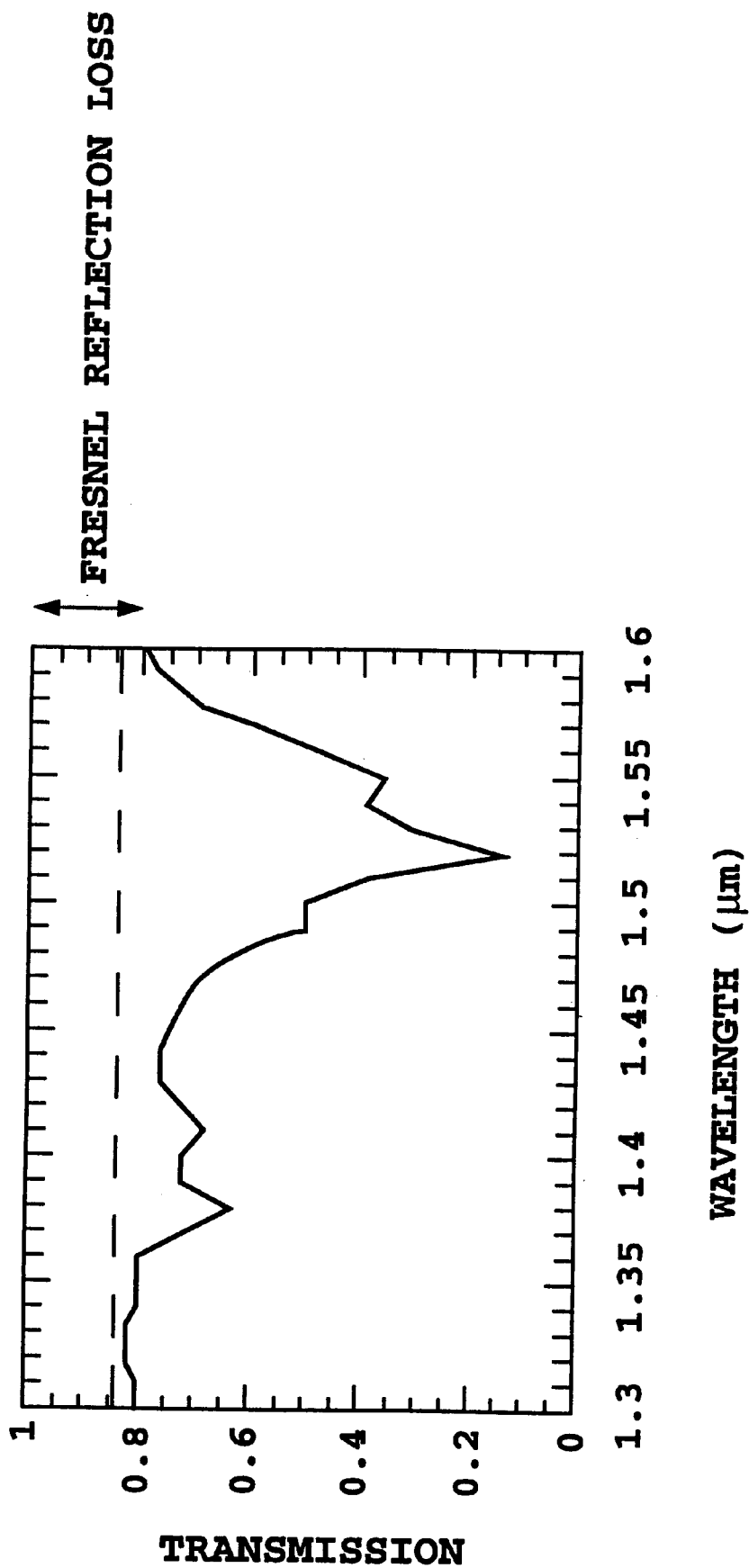
FIG. 5 is a graph showing absorption characteristics of the prior art AANP.
Figure 6:
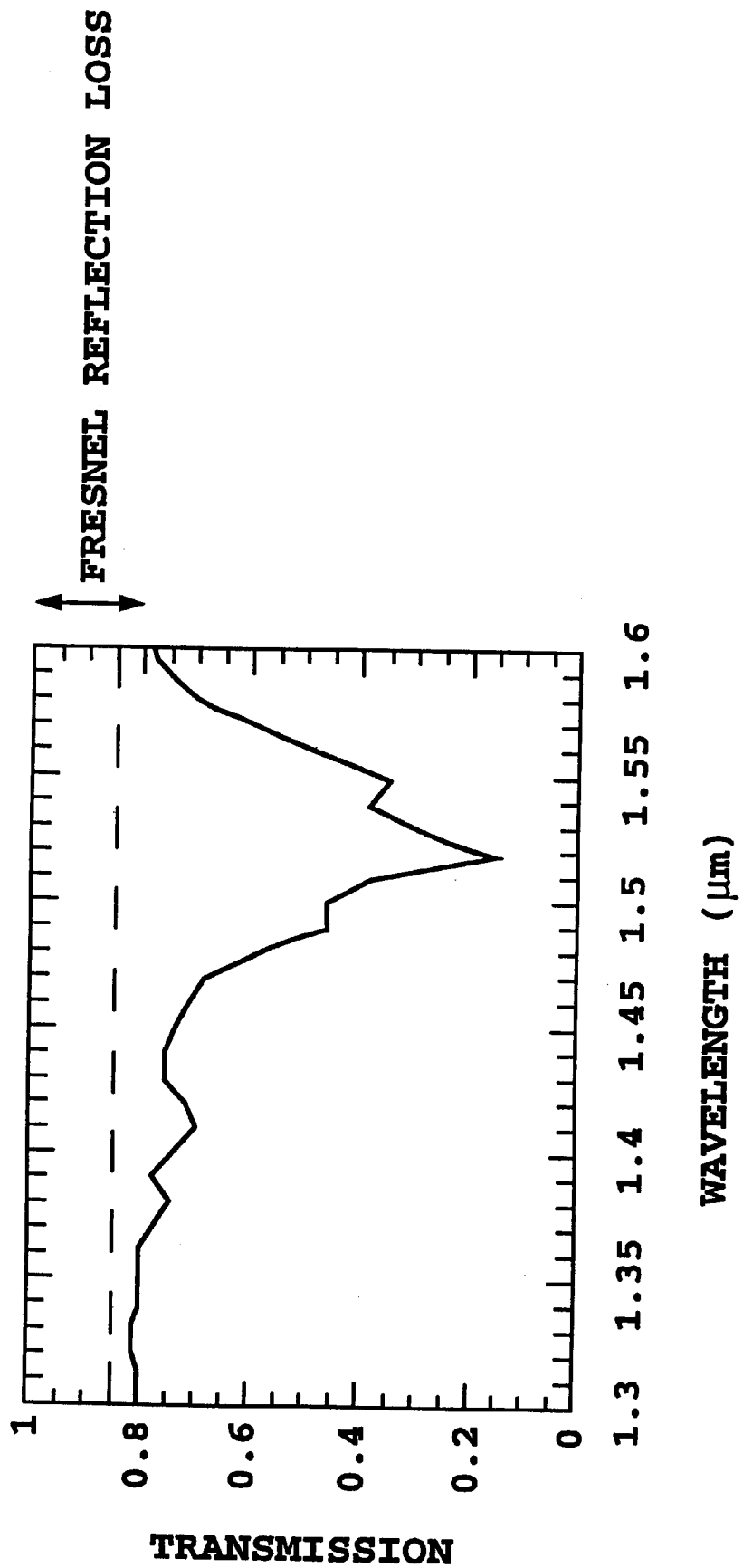
FIG. 6 is a graph showing absorption characteristics of AANP with hydrogen of the nitropyridine part deuterated.
Figure 7:
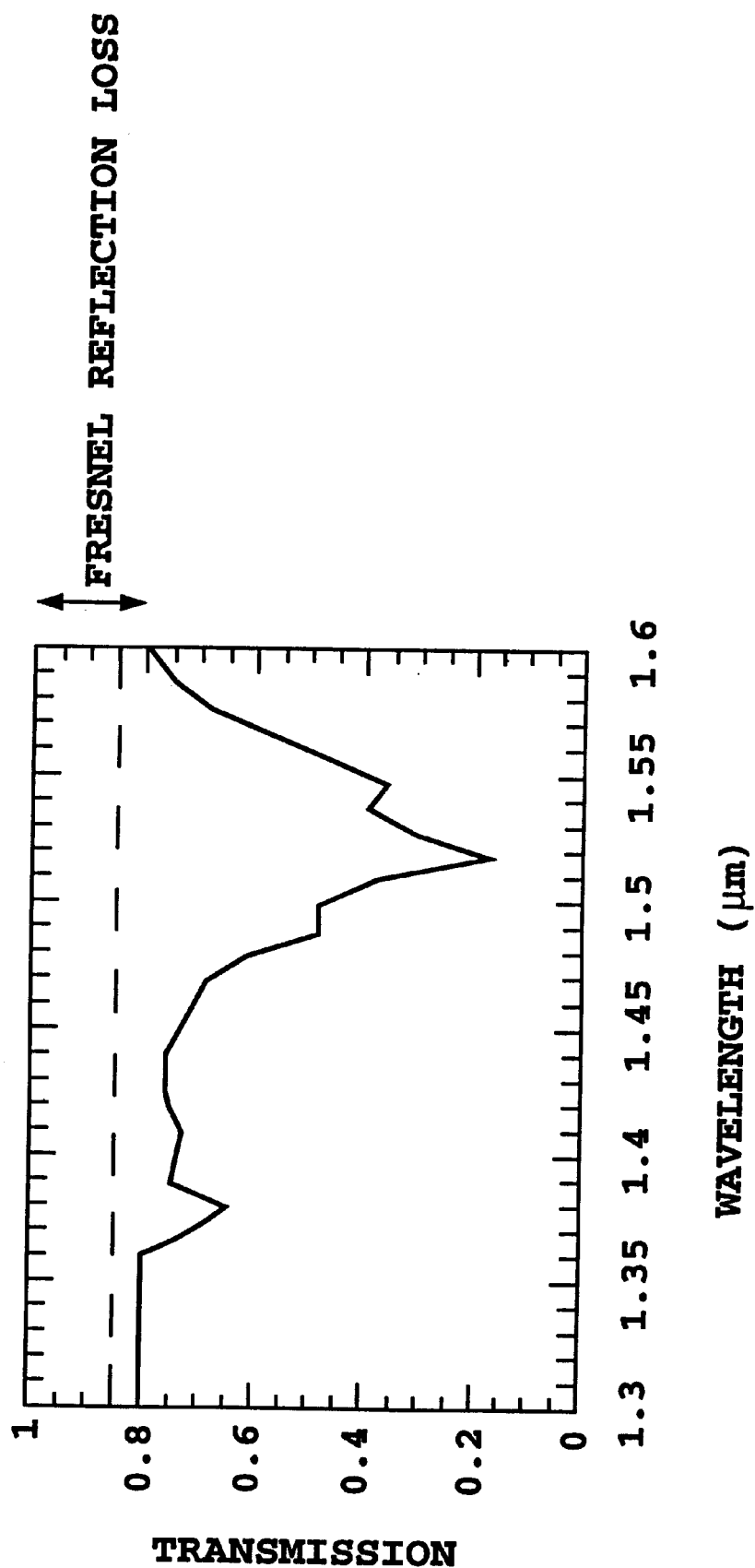
FIG. 7 is a graph showing absorption characteristics of AANP with hydrogen of the adamantane part deuterated.

Measurement results of absorption characteristics in the near-infrared region of these three types of AANP single crystals and the above-described AANP single crystal according to the present invention are shown in FIGS. 4 to 7. In the Figures, FIG. 4 shows the absorption characteristics of the AANP with hydrogen of N—H part deuterated according to the present invention, FIG. 5 shows the absorption characteristics of the prior art AANP, FIG. 6 shows the absorption characteristics of the AANP with hydrogen of the nitropyridine part deuterated, and FIG. 7 shows the absorption characteristics of the AANP with hydrogen of the adamantane part deuterated. In these measuements, 4 mm thick crystals were used as the samples.

tal sizes of deuterated AANP that could be produced are shown in Table 1. AANP with all the hydrogen of the nitropyridine part deuterated is particularly poor in crystallinity, and only a small crystal was obtained. Also, in AANP with all the hydrogen of the adamantane part deuterated, it was found that the deuteration adversely affects the crystallinity, and a large-sized crystal could not be obtained. On the other hand, in AANP with the N—H part deuterated, a crystal of the same characteristics was obtained as AANP not deuterium substituted in any rate. From the results, it has been found that deuteration of N—H part is effective for reducing absorption while maintaining the crystallinity of AANP.

When the wavelength conversion efficiency required is below $8 \times 10^{-4}$/W, it is not necessary to obtain a large-sized crystal. So, in addition to the deuteration of N—H part of the AANP, a part or all of the hydrogen of the nitropyridine part and/or the adamantane part may be substituted with deuterium.

TABLE 1

|  |  | crystal size (mm) | | |
| --- | --- | --- | --- | --- |
|  |  | 5 × 5 × 5 | 10 × 10 × 10 | 20 × 20 × 20 |
| Prior art AANP |  | E | E | E |
| Nitropyridine part deuterated AANP |  | G | P | P |
| Adamantane part deuterated AANP |  | G | G | P |
| N-H part deuterated AANP | substitution rate 25% | E | E | E |
|  | substitution rate 50% | E | E | E |
|  | substitution rate 75% | E | E | E |
|  | substitution rate 100% | E | E | E |

Note:
E: Excellent crystallinity
G: Good crystallinity
P: Crystallization impossible As shown in FIG. 5, conventional AANP has a strong absorption from 1.48 $\mu$m to 1.57 $\mu$m wavelength, including a main peak at 1.52 $\mu$m and sub-peaks at 1.50 $\mu$m and 1.55 $\mu$m wavelength. This absorption causes degradation of wavelength conversion characteristics relating to light at and around 1.55 $\mu$m wavelength. On the other hand, as shown in FIG. 4, in the AANP with hydrogen of N—H part deuterated according to the present invention, absorption from 1.48 $\mu$m to 1.57 $\mu$m wavelength, including the main peak at 1.52 $\mu$m and sub-peaks at 1.50 $\mu$m and 1.55 $\mu$m, is remarkably reduced, to less than 1/10 that of the conventional AANP. The reason why the absorption peak does not disappear completely is considered as due to the AANP with hydrogen of N—H part not deuterated since the content of the AANP with hydrogen of N—H part deuterated is about 95%. This shows that absorption at and around 1.55 $\mu$m can be considerably reduced by the AANP according to the present invention.

Further, as shown in FIGS. 6 and 7, the AANP with hydrogen of the nitropyridine part deuterated and the AANP with hydrogen of the adamantane part deuterated are almost the same as the conventional AANP in the absorption from 1.48 $\mu$m to 1.57 $\mu$m wavelength, showing that deuteration of the nitropyridine part or the adamantane part is ineffective for absorption reduction, and that deuteration of N—H part is effective.

Embodiment 2

A difference was noted in AANP crystallinity depending on a difference in the deuterium substitution position. Crys- Embodiment 3

Figure 8:
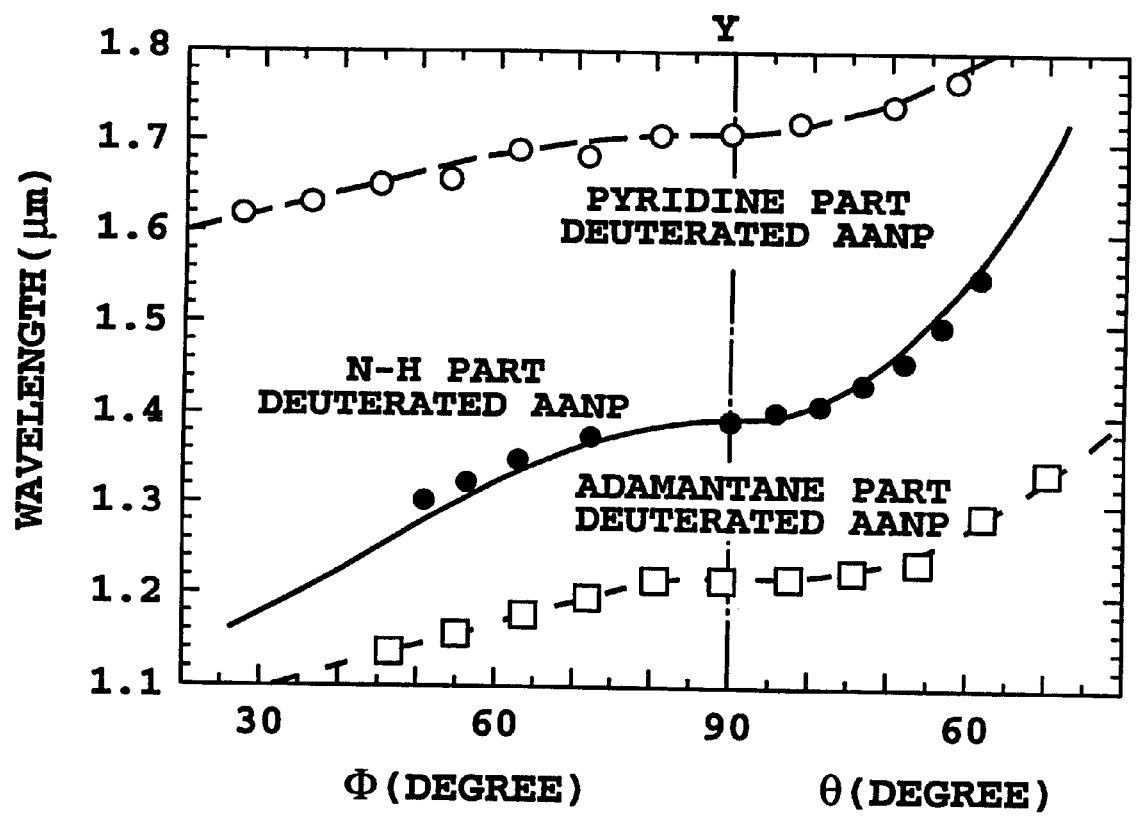
FIG. 8 is a graph showing the relationship between second harmonic generation (SHG) phase matching wavelength and crystal orientation of AANP with hydrogen of the nitropyridine part deuterated, AANP with hydrogen of the adamantane part deuterated, and AANP with hydrogen of the N—H part deuterated.

A difference was noted in phase matching wavelength depending on a difference of the deuterium substitution position. Phase matching wavelength is an important factor for determining the operative wavelength region when a nonlinear optical crystal is used as a wavelength conversion device. FIG. 8 shows the relationship between the SHG phase matching wavelength and crystal orientation of individual deuterium substituted AANPs. It was found that both AANP with all hydrogen of the nitropyridine part deuterated and AANP with all hydrogen of the adamantane part deuterated could not have the same applicability as the conventional AANP for SHG using 1.5 $\mu$m wavelength region as the fundamental light wavelength, and the wavelength conversion efficiency thereof remained lower. On the other hand, the AANP with hydrogen of N—H part deuterated was found to have the same phase matching characteristic as an AANP not deuterated at any substitution rate and to have the same applicability as the conventional AANP Although the wavelength conversion efficiency of the deuterated AANP is reduced by the shifting of the phase-matching characteristics, when the wavelength conversion efficiency is below about $8 \times 10^{-4}$/W, a part or all of the hydrogen of the nitropyridine part and/or the adamantane part may be substituted with deuterium.

According to the above Embodiments 1 to 3, it has been confirmed that the reduction of wavelength conversion efficiency in the 1.5 $\mu$m wavelength region in AANP, which has heretofore been a problem, can be solved by deuteration of hydrogen of at least N—H part of the AANP.

Incidentally, wavelength conversion is generally concerned with light of three wavelengths. In this case, there may be a case in which two of the three wavelengths are the same, and two wavelengths are concerned in the wavelength conversion. When, of the three wavelengths, even one wavelength is subjected to a large absorption loss in the medium, wavelength conversion efficiency as a whole will be substantially reduced. Conversely, as in the prior art AANP, one which is low in wavelength conversion efficiency concerned with light at and around 1.55 μm wavelength due to an absorption at and around 1.55 μm wavelength can be improved in wavelength conversion efficiency by deuteration of hydrogen atom of the amino part in the AANP according to the present invention.

Further, when the AANP is used as a nonlinear optical material, it is practically usable even though the hydrogen atom of N—H part is not deuterated for all of the AANP. That is, if the AANP with hydrogen atom of N—H part deuterated is partly contained in the prior art AANP, because the absorption at and around 1.55 μm wavelength is almost proportional to the content of the prior art AANP, the wavelength conversion efficiency can be improved as compared with the prior art AANP. Investigation of the content of the deuterated AANP has been conducted in Embodiment 6 which will be described later. As will be seen in Embodiment 6, a preferable content of the deuterated AANP in the organic nonlinear optical material comprised of the AANP according to the present invention is more than 25% by weight.

Embodiment 4

Figure 9:
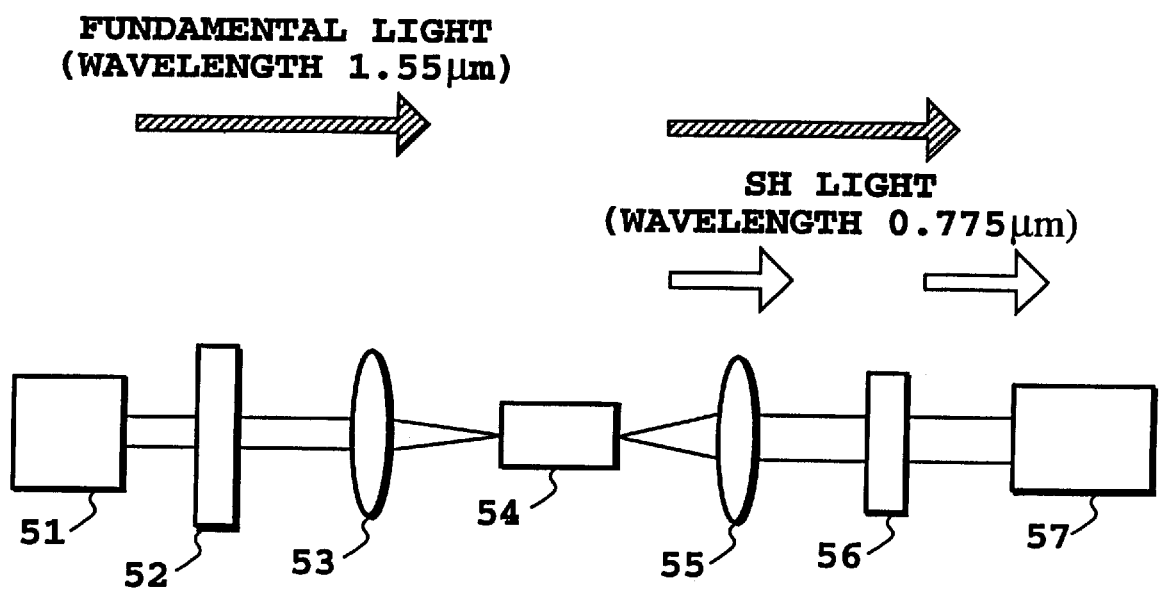
FIG. 9 is a schematic view showing the experimental setup of a SHG efficiency measurement used for evaluation in the present invention.

In this embodiment, the four types of AANP single crystals which were obtained in the embodiment 1 were measured for SHG efficiency at 1.55 μm wavelength using an experimental setup as shown in FIG. 9. In FIG. 9, the reference numeral 51 indicates a laser light source of 1.55 μm wavelength, 52 is a ½ wavelength plate, 53 is a lens, 54 is an AANP crystal, 55 is a lens, 56 is a wavelength filter, and 57 is a light detector. AANP single crystals were cut to have a phase matching orientation at 1.55 μm wavelength and a length was 4 mm. Normalized SHG efficiencies at 1.55 μm wavelength of the four types of AANP single crystals are shown in Table 2.

TABLE 2

Normalized SHG efficiency at 1.55 μm wavelength

| Material | Normalized SHG efficiency |
| --- | --- |
| AANP with hydrogen of N-H part deuterated of the present invention | $2.0 \times 10^{-3}$ (/W) |
| Prior art AANP | $2.0 \times 10^{-4}$ (/W) |
| AANP with hydrogen of nitropyridine part deuterated | $1.9 \times 10^{-4}$ (/W) |
| AANP with hydrogen of adamantane part deuterated | $2.0 \times 10^{-4}$ (/W) |

In the prior art AANP, the AANP with hydrogen of the nitropyridine part deuterated, and the AANP with hydrogen of the adamantane part deuterated, the normalized SHG efficiency at 1.55 μm was at most about $2 \times 10^{-4}$ (/W), whereas in the AANP with hydrogen of the N—H part deuterated according to the present invention, the normalized SHG efficiency at 1.55 μm was improved by more than 1 figure compared with that of the prior art AANP, achieving an efficiency of $2 \times 10^{-3}$ (/W). Further, the SHG efficiency in the wavelength region from 1.52 μm to 1.56 μm showed an improvement in efficiency at least by a factor of five.

From these results, it is apparent that the AANP according to the present invention provides a substantial improvement effect of wavelength conversion efficiency in wavelength conversion concerned with light at and around 1.55 μm wavelength.

The above comparative investigation shows the fact that absorption at and around 1.55 μm wavelength due to hydrogen of the N—H part degrades conversion efficiency of 2-adamantylamino-5-nitropyridine in the 1.55 μm wavelength region and demonstrates the effectiveness of the present invention.

As described above, since the organic nonlinear optical material containing the AANP according to the present invention considerably reduces absorption loss at and around 1.55 μm wavelength compared with the prior art organic nonlinear optical material AANP, it can provides substantial improvement in wavelength conversion efficiency concerned with light at and around 1.55 μm wavelength.

At and around 1.55 μm wavelength is one of optical communications wavelength region, where a demand is strong for highly efficient wavelength conversion devices such as those relating to wavelength division multiplexing transmission systems, and thus the present invention is of great value in optical communications and optical information processing areas.

Embodiment 5

Embodiment 5 shows a production method of deuterated AANP which differs from the production method shown in the above Embodiment 1.

The AANP of the present invention can similarly be obtained when, as the starting materials, 1-chloroadamantane is used in place of 1-adamantane with hydrogen of the amino group part deuterated, and 2-amino-5-nitropyridine with hydrogen of amino group part deuterated is used in place of 2-chloro-5-nitropyridine.

Further, AANP with more than 95% of hydrogen of N—H part deuterated could be obtained when undeuterated AANP was heat refluxed for about 2 weeks in a mixture (50:50) of THF and heavy water.

Embodiment 6

Embodiment 6 shows the relationship between the deuteration rate of AANP and a difference in SHG efficiency of the material.

Figure 10:
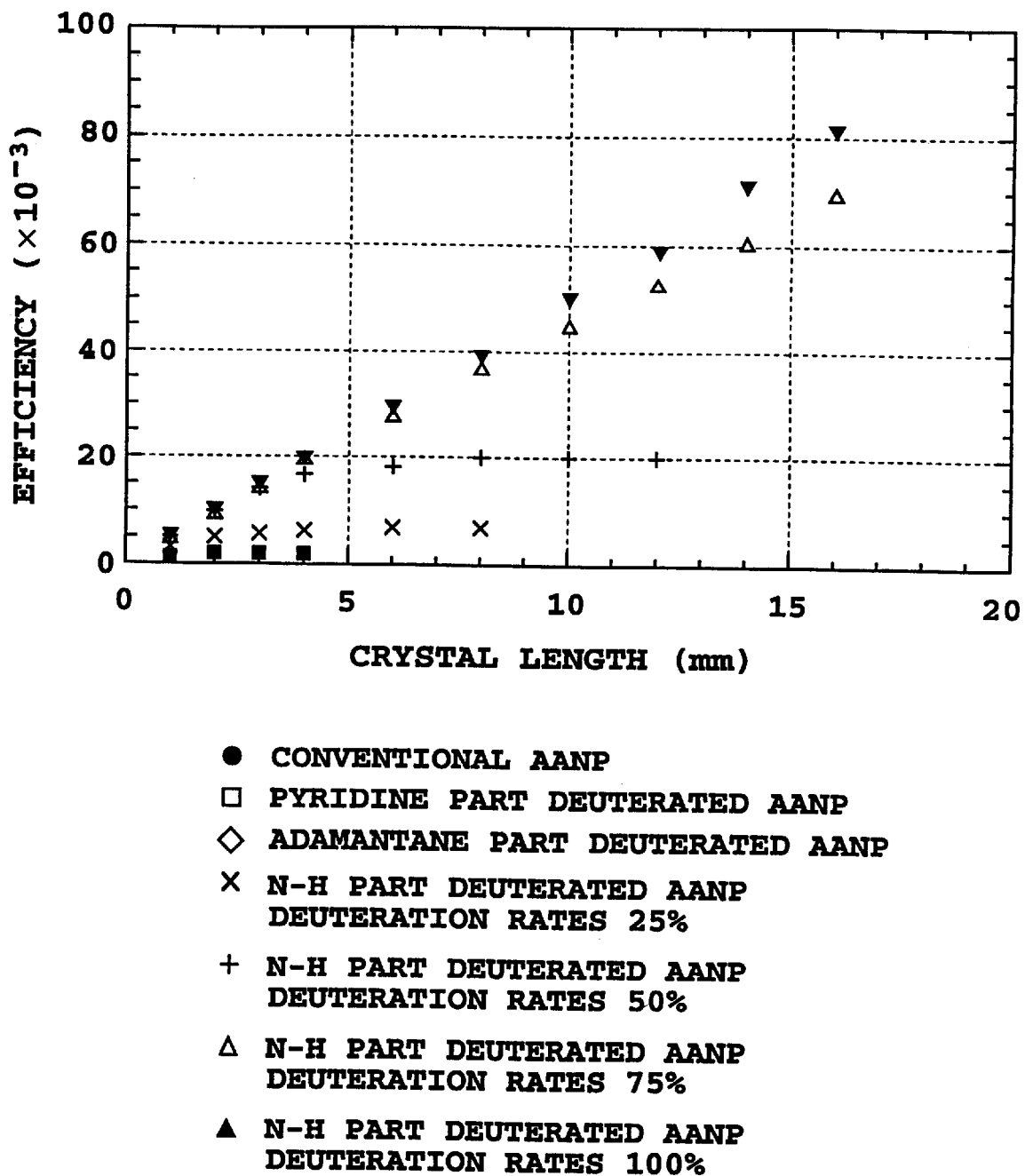
FIG. 10 is a graph showing dependence of SHG wavelength conversion efficiency on crystal length for AANP with hydrogen of the nitropyridine part deuterated, AANP with hydrogen of the adamantane part deuterated, and AANP with hydrogen of the N—H part deuterated with varied substution rate.

Using AANPs with different deuteration rate of hydrogen of N—H part, SHG wavelength conversion efficiency versus deuteration rate was measured. The incident light wavelength is 1.55 μm. At the same time, similar measurements were also made for the prior art AANP, AANP with all hydrogen of the nitropyridine part deuterated, and AANP with all hydrogen of the adamantane part deuterated. The results of measurement are shown in FIG. 10.

In the prior art AANP, AANP with all hydrogen of the nitropyridine part deuterated, and AANP with all hydrogen of the adamantane part deuterated, the wavelength conversion efficiency is saturated with a crystal length of about 2 mm, whereas in the AANP with hydrogen of N—H part deuterated, the wavelength conversion efficiency increases with increasing crystal length, the effect of deuteration on the wavelength conversion efficiency began to appear from a deuteration rate of 25%, and the wavelength conversion efficiency was as high as $2.0 \times 10^{-3}$ at a deuteration rate of 50%.

Further, in the AANP with 75% hydrogen of N—H part deuterated, saturation of wavelength conversion efficiency does not occur even with a length of 16 mm, which is the maximum crystal length of the present measurement, the conversion efficiency increasing to $7 \times 10^{-3}$. Similarly, in the AANP with 100% hydrogen of N—H part deuterated, no saturation occurs in the wavelength conversion efficiency even with the maximum crystal length in the present measurement of 16 mm, attaining a wavelength conversion efficiency of $8 \times 10^{-3}$.

From these results, it has been shown that effect of deuteration becomes conspicuous with AANP with more than 50% of hydrogen of N—H part deuterated. Still further, it has been known that a significant effect can be expected for wavelength conversion efficiency of an optical material when the deutration rate is higher than 25%.

The present invention has been described in detail with respect to preferred embodiments, and it will now be apparent form the foregoing to those skilled in the art that changes and modifications may be made without departing from the invention in its broader aspects, and it is the intention, therefore, in the appended claims to cover all such changes and modifications as fall within the true spirit of the invention.

What is claimed is:

1. 2-adamantylamino-5-nitropyrdine effective for use as a nonlinear optical material, wherein hydrogen of at least an N—H part of the 2-adamantylamino-5-nitropyrdine is deuterated in an amount effective for increasing wavelength conversion efficiency in a wavelength region of about 1.55 $\mu$m as compared to an adamantylamino-5-nitropyrdine that does not have hydrogen of its N—H group substituted with deuterium, at least about 25 weight percent of the 2-adamantylamino-5-nitropyrdine having a hydrogen of at least an N—H part deuterated.

2. 2-Adamantylamino-5-nitropyrdine according to claim 1 wherein only hydrogen of the N—H part of 2-adamantylamino-5-nitropyrdine is substituted with deuterium.

3. 2-Adamantylamino-5-nitropyrdine according to claim 1 wherein at least about 50 weight percent of the 2-adamantylamino-5-nitropyrdine has a hydrogen of its N—H part substituted with deuterium and the 2-adamantylamino-5-nitropyrdine has a wavelength conversion efficiency of at least about $2.0 \times 10^{-3}$ (/W) at a wavelength of about 1.55 $\mu$m.

4. 2-Adamantylamino-5-nitropyrdine according to claim 1 wherein at least about 75 weight percent of the 2-adamantylamino-5-nitropyrdine has a hydrogen of its N—H part substituted with deuterium and the 2-adamantylamino-5-nitropyrdine has a wavelength conversion efficiency of at least about $7.0 \times 10^{-3}$ (/W).

5. 2-Adamantylamino-5-nitropyrdine according to claim 1 wherein about 100 weight percent of the 2-adamantylamino-5-nitropyrdine has a hydrogen of its N—H group substituted with deuterium and the organic nonlinear optical material has a wavelength conversion efficiency of at least about $8.0 \times 10^{-3}$ (/W).

* * * * *